United States Patent
Lilly et al.

(10) Patent No.: US 8,219,418 B2
(45) Date of Patent: *Jul. 10, 2012

(54) CONTROLLED SUBSTANCE TRACKING SYSTEM AND METHOD

(76) Inventors: Ralph B. Lilly, Houston, TX (US); Jesse J. Bornfreund, Houston, TX (US); Jeffrey A. Anon, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/135,151

(22) Filed: Jun. 27, 2011

(65) Prior Publication Data

US 2011/0264469 A1  Oct. 27, 2011

Related U.S. Application Data

(63) Continuation of application No. 10/803,259, filed on Mar. 18, 2004, now Pat. No. 7,970,622.

(51) Int. Cl.
*G06Q 10/00* (2012.01)
(52) U.S. Cl. ................ 705/2; 705/3; 600/300
(58) Field of Classification Search ............ 705/2
See application file for complete search history.

(56) References Cited

U.S. PATENT DOCUMENTS

| | | | | |
|---|---|---|---|---|
| 5,737,539 A | * | 4/1998 | Edelson et al. | 705/3 |
| 6,687,676 B1 | * | 2/2004 | Denny | 705/2 |
| 6,859,780 B1 | * | 2/2005 | Cunningham | 705/3 |

* cited by examiner

*Primary Examiner* — Lena Najarian
(74) *Attorney, Agent, or Firm* — The Matthews Firm (57) ABSTRACT

A method for tracking prescriptive medications is provided whereby a complete prescriptive medication history including active and inactive prescriptive medications is stored for a plurality of patients utilizing a plurality of pharmacies wherein the pharmacies may be affiliated or unaffiliated. The information may be selectively retrieved through a secure computer connection by entities such as hospitals, doctors, pharmacies, insurance companies, government agencies and the like. The information may be utilized to benefit the patient whereby a doctor is able to obtain an accurate view of the complete prescriptive medication history of the patient including prescriptive medications by other doctors. Hospitals will be able to obtain, in accord with the invention, a prescriptive medication history prior to treatment such as emergency treatment where such information is not normally available. The stored data for each prescriptive medication transaction includes searchable data such as the patient's name, address, doctor, pharmacy, aberrant use flag, and the like.

7 Claims, 2 Drawing Sheets

CONTROLLED SUBSTANCE TRACKING SYSTEM AND METHOD

CROSS REFERENCE TO RELATED APPLICATION

This application claims the benefit of U.S. Provisional Application No. 60/332,807 filed on Nov. 14, 2001, and claims the benefit of U.S. application Ser. No. 10/062,251 filed Jan. 31, 2002, and claims the benefit of and is a continuation of U.S. application Ser. No. 10/803,259, filed Mar. 18, 2004, now U.S. Pat. No. 7,970,622 issued Jun. 28, 2011, the entirety of which is incorporated herein by reference.

FIELD

The present invention relates generally to methods for tracking controlled substances and, more specifically, to methods especially suitable for tracking and managing prescription information in aggregate.

BACKGROUND

Although the exact frequency of prescription drug abuse is unknown in the United States, it has been reported that more than fifty percent of all emergency room visits for drug-related problems are connected to prescription drug misuse or accidental overdose. It has also been estimated that in some communities, more than sixty percent of medical examiner cases are related to prescription drugs.

It is estimated that more than four million people a year in the U.S. misuse or abuse prescription drugs. For instance, according to an August 1999 article in the Journal of the American Geriatrics Society, older Americans (age 65 and older) currently account for 12.5% of the total US population, but consume 25% of all prescription medications. It is documented that 17% of the senior population misuses medications, accounting for approximately $2 billion loss annually.

The AMA estimates that 5% of physicians are grossly negligent and 1-1.5% are dishonest in their prescribing of pharmaceuticals. This would amount to a cost of $2.5 billion annually.

Three hundred fifty thousand adverse medication errors (probably far greater not reported) occur each year among one-half million nursing home residents in the United States. One employee in ten has a problem with alcohol/drugs. Absenteeism is 66% higher among drug users.

Among drug users, health benefit utilization is 300% higher, disciplinary actions are 90% higher, and employee turnover is significantly higher. Forty-seven percent of workplace accidents are drug related.

In fact, it is clear that the Healthcare industry is facing a number of challenges today unlike ever faced before. An educated, consuming public has ever increasing expectations for exponential improvement in healthcare delivery, while at the same time, economic pressures are forcing tighter controls over cost, efficiency and quality.

The industry has widely recognized a need for better efficiencies, but without notable success in many areas, including prescription abuse. For instance, the Healthcare Information Portability and Accountability Act (HIPAA) mandates making the exchange of information more ubiquitous, secure, and efficient but does not provide a solution with respect to prescription tracking and abuse. While it is well known that it would be desirable to reduce spiraling cost structures, mitigate health risks, provide more efficient billing and business modeling, eliminate redundancy, and improve informational flow, the solutions to such overwhelming problems are generally unavailable.

In 1993, prescription drug sales were $25 billion. Since that time prescriptions have risen more than 50%, totaling close to three billion prescriptions annually. With soaring costs, the sum of prescription drugs is currently greater that $50 billion annually, with limited ability to control or manage those costs.

These estimates are only for the cost of drugs themselves, and don't include many of the highly significant tangential costs associated with abuse, additional healthcare requirements and costs associated with drug interactions, insurance fraud resulting from purchase of class drugs for resale on the street, dispensing of wrong prescriptions due to misread prescriptions, and the like, which are proportionally of greater cost.

It would be desirable to provide a healthcare utility that can assist substantially in reducing these misused and abused prescriptions. It would be desirable to provide major changes in the delivery of prescription drugs that produce measurable social and economic impacts on spending within the healthcare value chain including less abuse-related healthcare costs, fewer erroneous prescriptions, more accountability, and better tracking and management of prescriptions.

Patents that involve attempts to solve the above or related problems include the following:

U.S. Pat. No. 6,067,524, issued May 23, 2000, to Byerly et al., discloses a method and system for generating advisory messages to pharmacy patients that includes appending patient-specific information to a data record containing normally transmitted information. The data record is transmitted between a third party computer and a pharmacy computer during a pharmacy transaction. The data record transmitted to the pharmacy computer is captured by an advisory computer as the data record is received by the pharmacy computer or after the data record is transmitted to the pharmacy computer, and the patient-specific information is extracted from the captured data record. The advisory computer generates an advisory message based on the extracted patient-specific information, and it transmits the generated advisory message to a pharmacy printer. The advisory computer includes a memory containing a data structure for storing the patient-specific information, the normally transmitted information, and the generated advisory message. A computer program product includes a computer storage medium and a computer program code mechanism embedded in the computer storage medium for causing a computer to generate an advisory message. The computer program code mechanism includes a first computer code device configured to append the patient-specific information, a second computer code device configured to capture the data record transmitted to the pharmacy computer, a third computer code device configured to extract the patient-specific information from the captured data record, a fourth computer code device configured to generate the advisory message based on the extracted patient specific information, and a fifth computer code device configured to transmit the generated advisory message to the pharmacy printer.

U.S. Pat. No. 6,055,507, issued Apr. 25, 2000, to D. W. Cunningham, discloses a new and improved method of dispensing, tracking and managing pharmaceutical product samples by communicatively linking prescribers and pharmacies to a central computing station. The method entails utilizing product trial media that is exchanged for actual pharmaceutical product. The media is encoded with information that identifies a particular pharmaceutical trial product, such as by magnetic encoding similar to that used with credit cards. The media is distributed to participating medical doctors or prescribers who then activate the media via the central computing station. The prescriber then transfers the activated media to patients who then present the media to participating pharmacies. Before filling the pharmaceutical trial product identified by the media, the pharmacy validates the media via a link with the central computing station. Then, the pharmacy dispenses the prescribed pharmaceutical trial product. The central computing station also includes a database that records data related to the use of the media so that all pharmaceutical trial products can be accounted for.

U.S. Pat. No. 5,542,420, issued Aug. 6, 1996, to Goldman et al., discloses a health care system for specifying edibles to individual subjects. The personalized method and system for storage, communication, analysis and processing of health-related data comprises a storage containing data relating to health and edibles and is adapted to receive data on the conditions and characteristics of the individual subjects. The health care system further comprises input terminals adapted to be coupled to the storage means for providing data on the conditions and characteristics of the individual subjects, and a health computer for correlating the data relating to health and edibles with the data on the condition and characteristics of an individual subject to provide a personalized prescription of edibles.

U.S. Pat. No. 5,628,530, issued May 13, 1997, to G. B. Thornton, discloses a method and system for collectively tracking demographics of physician prescribed starter drug samples dispensed to a plurality of patients from a plurality of different dispensing locations employs a multipart product specific sample drug voucher, such as a smart card or a pre-printed two part voucher, which has a marketing information portion and a separable prescription portion to be completed by the prescribing physician with starter drug sample quantity and dosage information along with patient demographic information. The prescription portion is segregated from the marketing information portion at the pharmacy either electronically by a card reader, if it had been encoded on a smart card by the physician, or physically by separation along a perforation, if recorded on a two part voucher, and is electronically retrievably stored in the pharmacy computer from where this tracking information is electronically transmitted to a central remote computer, such as at the drug manufacturer, for subsequent rapid market analysis.

U.S. Pat. No. 5,737,539, issued Apr. 7, 1998, to Edelson et al., discloses an electronic prescription creation system for use by professional prescribers at the point of care which has a prescription division subsystem permitting creation of a single prescription to be automatically divided into two components for fulfillment of one portion quickly and locally at higher cost and of another portion by remote mail order taking more time but providing a cost saving for a major part of the prescription. The prescription creation system has an ability to access remote source databases for system presentation to the prescriber of relevant, authorized and current drug, drug formulary and patient history information, with dynamic creation of a transient virtual patient record, the information being presented to the prescriber before completion of the prescription, permitting enhancement of the quality of prescribing decisions.

U.S. Pat. No. 5,758,095, issued May 26, 1998, to Albaum et al., discloses a system and method for ordering and prescribing drugs for a patient. This system includes an improved process for facilitating and automating the process of drug order entry. The user may interact with the system in a variety of ways such as keyboard, mouse, pen-base entry or voice entry. The system includes a database containing medical prescribing and drug information which is both general and patient-specific. The system also permits the user to view current and previously prescribed medications for any patient. The system can alert the user to potentially adverse situations as a result of the prescribed medication based on information in the database. The system also can automatically determine product selection based on descriptions and can automatically communicate the order to a pharmacy. Further, the system includes a means for automatically displaying messages to the user relating to predetermined situations. For example, such situations may include a medication which is not available in the formulary or the prescription of a non-recommended medication. The system streamlines the order entry process and makes information important to the drug ordering process easily available.

U.S. Pat. No. 5,845,255, issued Dec. 1, 1998, to C. Mayaud, discloses a wirelessly deployable, electronic prescription creation system for physician use that captures into a prescription a patient condition-objective of the prescribed treatment and provides for patient record assembly from source elements, with privacy controls for patient and doctor, adverse indication review and online access to comprehensive drug information including scientific literature. Extensions to novel multi-drug packages and dispensing devices, and an "intelligent network" remote data retrieval architecture as well as onscreen physician-to-pharmacy and physician-to-physician e-mail are also provided.

U.S. Pat. No. 5,991,731, issued Nov. 23, 1999, to Colon et al., discloses a computer system and method for managing data used in conducting clinical studies concerning subjects at a plurality of participating, geographically distributed clinical sites, wherein each participating clinical site having a computer or inputting, transmitting and receiving data over the Internet. An Internet network server computer is interfaced to a database host computer through a private network. The system communicates data over the Internet to determine patient eligibility, randomization and initial prescriptions, which can then be adjusted by the physician online. The final prescription is printed out for signature and sent electronically to a distribution center. Study data is maintained in a database in the host computer behind a firewall provided in the Internet server computer.

U.S. Pat. No. 5,832,449, issued Nov. 3, 1998, to D. W. Cunningham, discloses a new and improved method of dispensing, tracking and managing pharmaceutical product samples by communicatively linking prescribers and pharmacies to a central computing station. The method entails utilizing product trial media that is exchanged for actual pharmaceutical product. The media is encoded with information that identifies a particular pharmaceutical trial product, such as by magnetic encoding similar to that used with credit cards. The media is distributed to participating medical doctors or prescribers who then activate the media via the central computing station. The prescriber then transfers the activated media to patients who then present the media to participating pharmacies. Before filling the pharmaceutical trial product identified by the media, the pharmacy validates the media via a link with the central computing station. Then, the pharmacy dispenses the prescribed pharmaceutical trial product. The central computing station also includes a database that records data related to the use of the media so that all pharmaceutical trial products can be accounted for.

U.S. Pat. No. 6,068,156, issued May 30, 2000, to Liff et al., discloses an automated drug dispensing system that includes a cabinet adapted to store a variety of prepackaged pharmaceuticals in a plurality of bins for filling patient prescriptions. Each bin stores a particular variety of packaged multiple-dose pharmaceutical. Each variety of pharmaceutical is associated with a particular code. A controller receives request signals and in response generates dispense signals. Each bin includes a dispenser coupled to the controller for dispensing the packaged pharmaceuticals therefrom in response to a dispense signal sent from the controller. After a package is dispensed, a code reader determines the code of the dispensed package and verifies whether the code on the dispensed package matches the code of the requested package.

U.S. Pat. No. 6,073,106, issued Jun. 6, 2000, to Rozen et al., discloses a method whereby via Internet communications or via phone/fax/mail, a participant is prompted to provide a constant identifier and a selected password. Emergency and confidential categories of medical information are identified, and the participant is prompted to provide personal information in each of the categories and a different personal identification number (E-PIN, C-PIN) for each category. The participant is also prompted to provide an instruction to disclose or to not disclose the personal information in the emergency category in the event a requester of the information is an emergency medical facility and is unable to provide the participant's E-PIN. Alteration of any of the participant's medical information is enabled upon presentation of the participant's identifier and password by the requester. The emergency information or the confidential information is disclosed upon presentation of the participant's identifier and E-PIN or C-PIN. In addition, the emergency information is disclosed to an emergency medical facility verified as such by a service provider in the event the participant has provided an instruction to disclose the emergency information. Storage and access to health related documents such as healthcare power of attorney, consent for treatment, and eyeglass prescription is also provided.

U.S. Pat. No. 6,128,620, issued Oct. 3, 2000, to Pissanos et al., discloses a medical database and associated methods especially suited for compiling information in a medical malpractice situation. A general medical database is provided and specific medical information corresponding to a given situation is entered. Entry of the information automatically cross-references some terms of the entered data to definitions in the general medical database. Terms are readily looked up when reviewing specific medical information and definitions are easily inserted where desired. A drug reference display provides two-way lookup from drugs to their side effects (or contraindications or interactions) and back. Significant information from an entered medical chronology is easily copied to a significant information section when a reviewer finds the information important.

U.S. Pat. No. 6,195,612, issued Feb. 27, 2001, to T. L. Pack-Harris, discloses a pharmacy benefit management system that includes a pharmacy computer for generating pharmacy claim information based on pharmacy activity of a medical group. A health plan computer is responsive to the pharmacy claim information for generating pharmacy activity information for the medical group. A medical group computer receives the pharmacy activity information from the health plan computer and stores the pharmacy activity information. The pharmacy activity information is processed to generate utilization information to enable the medical group to monitor the pharmacy activity.

U.S. Pat. No. 6,216,104 B1, issued Apr. 10, 2001, to Mosfeghi et al., discloses a Computer-based Patient Record (CPR) system including user equipment devices which are configured for speech synthesis in response to speech markup language text and which are connected via a network to a middle tier of a server system. The CPR system further includes a message delivery facility for delivery of textual messages to any of pager, electronic mail, or voice mail (after text-to-speech synthesis) message delivery vehicles. The server system accesses a user specific data store containing speech synthesis profiles which include prosodic information of the voices and speech of users, and message delivery profiles which specify which of the aforementioned message delivery vehicles are to be used and in what order. The stored speech synthesis information associated with an originator of a message and the stored message delivery information associated with the recipient of message are provided by the server to user equipment or a reminder generator to produce speech markup files containing information needed to synthesize the vocal and speech characteristics of the originator accompanied by delivery instructions reflecting the message delivery preferences of the recipient.

U.S. Pat. No. 6,219,674 B1, issued Apr. 17, 2001, to J. B. Classen, discloses systems and methods for creating and using product data to enhance the safety of a medical or non-medical products. The systems receive vast amounts of data regarding adverse events associated with a particular product and analyze the data in light of already known adverse events associated with the product. The system develops at least one proprietary database of newly discovered adverse event information and new uses for the product and may catalog adverse event information for a large number of population sub-groups. The system may also be programmed to incorporate the information into intellectual property and contract documents. Manufacturers can include the information in consumer product information, which they provide to consumers or, in the case of certain medical products, prescribers of the medical products.

U.S. Pat. No. 6,230,142 B1, issued May 8, 2001, to Benigno et al., discloses systems useful for analyzing data related to clinical pathways and performing actions based upon the analyses. A self-analyzing system for suggesting default clinical pathways for various procedures. A self-analyzing system for suggesting deviation from a current clinical pathway and entry into an alternative clinical pathway based upon historical information about the results of actions, statistical analysis systems based on the clinical pathways, a rating system for care providers or proposed pathways based on historical information, systems for gathering clinical pathway information, systems for tracking clinical pathway outcomes based on data collected post-treatment, a system for prequalification for appropriate discharge and post-discharge handling of and communication with a new class of patient, those requiring stable acute care, and a questionnaire computer language and subsystem are used in various stages of the systems disclosed. Corresponding methods are also disclosed.

U.S. Pat. No. 6,283,322 B1, issued Sep. 4, 2001, to Liff et al., discloses an automated drug dispensing system that includes a cabinet adapted to store a variety of prepackaged pharmaceuticals in a plurality of bins for filling patient prescriptions. Each bin stores a particular variety of packaged multiple-dose pharmaceutical. Each variety of pharmaceutical is associated with a particular code. A controller receives request signals and in response generates dispense signals. Each bin includes a dispenser coupled to the controller for dispensing the packaged pharmaceuticals therefrom in response to a dispense signal sent from the controller. After a package is dispensed, a code reader determines the code of the dispensed package and verifies whether the code on the dispensed package matches the code of the requested package.

U.S. Pat. No. 6,240,394 B1, issued May 29, 2001, to Uecker et al., discloses a system for generating targeted advisory messages for pharmacy patients based on selected monitored data components of each transaction. When a pharmacy computer prints transaction data, the system monitors the data using printer data capture hardware interposed between the pharmacy computer and its printer. An additional processor compares selected components of the monitored transaction data with preselected combinations of the components in a database. The database associates the preselected combinations of transaction data components with advisory message components retrieved from the database and used to build an advisory message for output to a printer, which may be the pharmacy computer or an additional printer. Targeting of the advisory messages is based on selected combinations of the identity of the drug being dispensed to the patient, the patient's age and gender, the new or renewal status of the prescription, and the identity of the party primarily responsible for payment to the pharmacy for the transaction.

The above-cited patents do not solve the problem of misused and abused prescriptions discussed above. Consequently, there remains a need for an improved system for tracking prescription drugs and/or controlled substances. Those of skill in the art will appreciate the present invention, which addresses the above, and other problems.

SUMMARY

An objective of the present invention is to provide an improved method for controlling information related to controlled substances and/or prescriptive medications.

Another objective of the present invention is to provide a complete prescriptive medication history of patients for use by doctors, hospitals, pharmacists, and other health care workers.

Another objective of the present invention is to provide a means for searching massive amounts of data for selected criteria to reduce costs involved with prescriptive medications.

These and other objectives, features, and advantages of the present invention will become apparent from the drawings, the descriptions given herein, and the appended claims. However, it will be understood that the above-listed objectives of the invention are intended only as an aid in quickly understanding aspects of the invention, and are not intended to limit the invention in any way, and therefore do not form a comprehensive or restrictive list of objectives, and/or features, and/or advantages.

Accordingly, the invention comprises, in one embodiment thereof, a method for tracking prescriptive medications. The method may comprise one or more steps such as, for instance, providing respective computer connections to a plurality of entities wherein the plurality of entities may comprise a plurality of unaffiliated and/or affiliated pharmacies, storing pharmaceutical computer data relating to prescriptive medication purchases obtained by a plurality of prescriptive medication purchasers from the plurality of unaffiliated pharmacies, and selectively transferring the pharmaceutical computer data through the computer connections to at least one of the plurality of entities for obtaining a medication history of a selected prescriptive medication purchaser for all prescriptive medications purchased by the selected prescriptive medication purchaser from all of the plurality of unaffiliated pharmacies based on the transferred pharmaceutical computer data.

The method may further comprise providing that the at least one of the plurality of entities comprises a physician's office and the selected prescriptive medication purchaser is a patient of the physician such that the physician's office utilizes the pharmaceutical computer data to verify the medication history of the selected prescriptive medication purchaser.

Other steps may further comprise providing that the at least one of the plurality of entities comprises a pharmacy with a pharmacist, such that when the selected prescriptive medication purchaser requests that the pharmacist fill a new prescriptive medication then the pharmacist utilizes the pharmaceutical computer data to compare the new prescriptive medication with respect to the medication history of the selected prescriptive medication purchaser. The method may further comprise the pharmacist accepting or declining to fill the new prescriptive medication based on the medication history.

Other steps may further comprise providing that at least one of the plurality of entities comprises a hospital and the selected prescriptive medication purchaser is a patient of the hospital such that the hospital utilizes the pharmaceutical computer data to determine the medication history of the selected prescriptive medication purchaser.

The method may further comprise providing that the pharmaceutical computer data for each of the prescriptive medication purchases comprises a name of a respective prescriptive medication purchaser, an address of the respective prescriptive medication purchaser, a drug prescribed, the respective prescriptive medication purchaser, a quantity of the drug, a dosage of the drug, a pharmacist name, and a doctor name.

The method may further comprise searching the stored pharmaceutical computer data based on one or more of the name of a respective prescriptive medication purchaser, the address of the respective prescriptive medication purchaser, the drug prescribed, the respective prescriptive medication purchaser, the quantity of the drug, the dosage of the drug, the pharmacist name, and the doctor name.

Other steps may further comprise storing pharmaceutical data related to whether a request for filling a prescriptive medication is filled or declined and/or providing that at least one of the plurality of entities comprises a government agency and/or storing pharmaceutical computer data relating to aberrant use of prescriptive medications.

The method of claim may further comprise providing that the plurality of entities may comprise a plurality of hospitals, a plurality of doctors, and at least one government agency, and selectively transferring the pharmaceutical computer data through the computer connections to at least one of the plurality of hospitals, the plurality of doctors, or the at least one government agency.

This summary is not intended to be a limitation with respect to the features of the invention as claimed, and this and other objects can be more readily observed and understood in the detailed description of the preferred embodiment and in the claims.

BRIEF DESCRIPTION OF THE DRAWINGS

For a further understanding of the nature and objects of the present invention, reference should be had to the following detailed description, taken in conjunction with the accompanying drawings, in which like elements are given the same or analogous reference numbers and wherein.

While the present invention will be described in connection with presently preferred embodiments, it will be understood that it is not intended to limit the invention to those embodiments. On the contrary, it is intended to cover all alternatives, modifications, and equivalents included within the spirit of the invention.

DESCRIPTION OF THE EMBODIMENTS

In accord with the method of the present invention, a secure, private, independent, network-based, centralized method operable for tracking and managing prescriptive medication information in aggregate is provided which allows electronic querying and real-time notification of patients' prescriptive medication history at the time of prescriptive medication creation. According to the method of the invention, this information is accessible within a controlled and appropriate context for use by healthcare professionals involved in the delivery of care to that patient.

Figure 1:
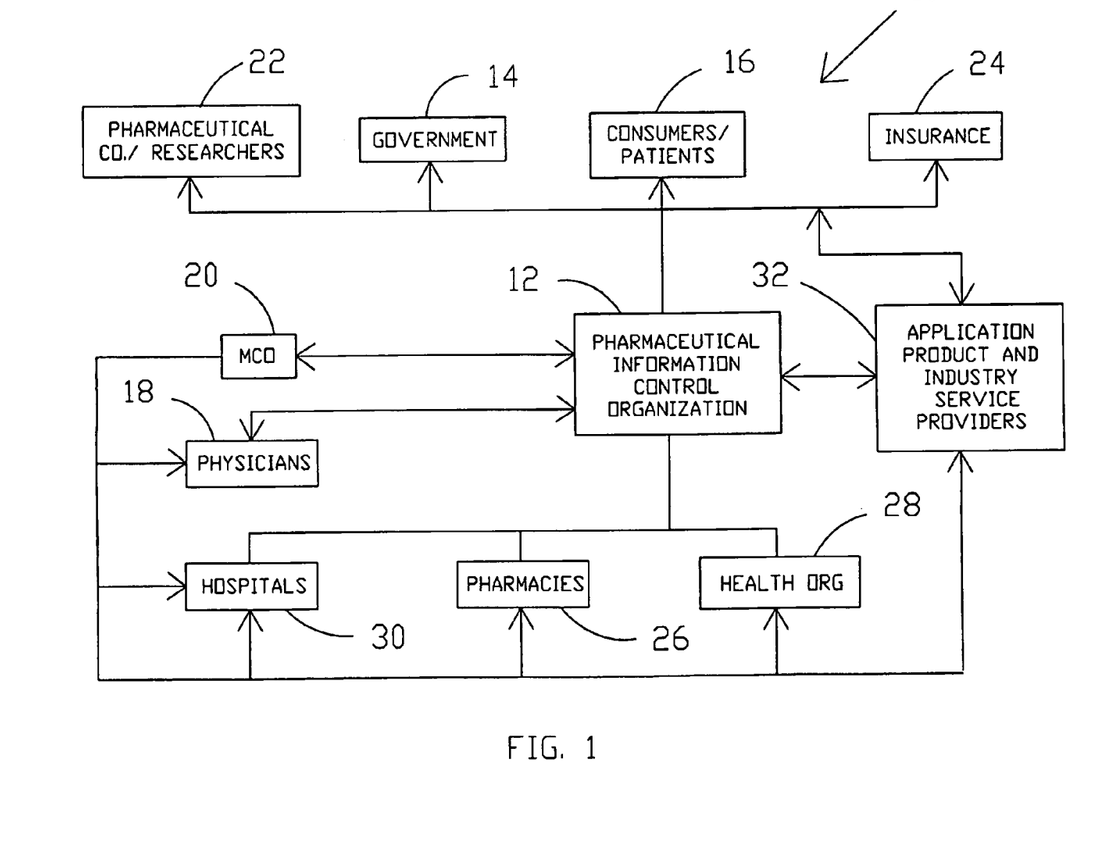
FIG. 1 is a block diagrammatic view showing an organization interconnection structure in accord with the present invention.

Referring now to the drawings and, more particularly to FIG. 1, there is shown one possible computer interconnection arrangement 10 between various entities/organizations and pharmaceutical information control organization 12 that may be utilized to implement the method of the present invention. Pharmaceutical information control organization 12 may be implemented as an independent information utility that acts as the central service center for the management of prescriptive medication drugs. By allowing ready access to appropriate information at various points within the prescriptive medication process, pharmaceutical information control organization 12 helps to protect the patient from a variety of potential risks associated with the prescribing of drugs and creates an audit capability that can help protect the healthcare professional, while eliminating significant financial overspending due to information gaps and misuse. Pharmaceutical information control organization 12 may be effectively operated utilizing different types of organization structures, e.g., for-profit business entity, nonprofit business entity, and the like. Pharmaceutical information control organization 12 may be monitored as desired using any suitable oversight group, e.g., a representative group from the various healthcare value chain members to ensure acceptable levels of information security, access and protection. Pharmaceutical information control organization 12 may be created as an independent, nonaffiliated entity to act as the information liaison between all members of the healthcare community.

Many different types of entities/organizations may be electronically interconnected in accord with the present invention with respect to pharmaceutical information control organization 12. The types of data available to each organization may be filtered depending on the type of organization/entity and the need thereof for the various types of pharmaceutical information available from pharmaceutical information control organization 12.

Consumers and patients 16 get the most benefit from the present invention. They will have a comfort knowing that their physician and other healthcare professionals involved in their care will have secure and private access to historical information about their active and inactive prescriptive medications that can create problems or interactions. Pharmaceutical information control organization 12 will permit consumers and their physicians to better manage the patient's prescriptive plan, lessening risk of misuse and counter indications. If desired, consumers may have access only to their own pharmaceutical records. Schedules of use may be provided and means for tracking, such as reminders, clocks, and so forth may be provided. If desired, consumers may provide feedback through pharmaceutical information control organization 12 as to the patient's perceived condition that may be accessed by physicians 18, pharmaceutical drug companies and/or research organizations 22 interested in drug efficacy, managed care organizations 20, and the like.

Government oversight entities 14, such as the DEA, FBI, CDC, and so forth, may be able to utilize data as required to reach the organization goals and within the limitations required therefore. For instance, the DEA may review data to determine areas where violations may be occurring. Presently, legal regulations may require that each time a prescriptive medication is filled that a paper copy of the transaction is forwarded to the DEA. However, compiling and using such data, which may involve billions of transactions, is overwhelming governmental manpower availability and results in high manpower costs with reduced investigative overview capability. Moreover, pharmacies waste manpower and time filling out and filing such papers. Government agencies such as the DEA, FBI, Veterans Administration Medical System, National Institute of Health, and the like, will find new efficiencies by utilizing the present invention. Even the pending new Medicare Programs, which include Pharmaceutical programs, can be brought to public availability with the comprehensive management support that is lacking today. The present invention removes many of the management limitations that affect such efficiencies and will help control costs of program delivery. All of these entities can have immediate access to potential medication abuse by identification of needless prescription duplications, potential drug interactions, and multi-source interstate prescriptive medication abuse. The system of the present invention may be utilized to recognize fraudulent prescriptive medications, geographically track selected drug purchases as may be desired in tracking disease spread, track purchases related to security investigations such as use of antidotes for certain bioweapons, track pharmaceutical purchase for other investigative reasons, obtain feedback from prescriptive medication users as discussed subsequently, and/or provide many types of information and statistics not presently available today.

Pharmaceutical companies and researchers 22 are in a constant race to provide the public with pharmacological formulations that are compatible with constantly evolving therapeutic formulations, and whose availability is being accelerated by the rapid expansion of effective clinical trials and research protocols. The pharmaceutical industry's ability to respond effectively to the competitive as well as regulatory demands is challenging because of the difficulty in realizing real or near term information access and tracking information. This responsibility requires an ongoing current database of pharmaceutical demands, immediate identification of adverse reactions, and recognition of the costly development of redundant pharmaceutical products. Pharmaceutical information control organization 12 provides the pharmaceutical industry with a vehicle to help them track and access appropriate information about prescriptive drugs. Pharmaceutical information control organization 12 provides the pharmaceutical industry with services which will assist in better planning, real time assessment and forecasting of regional pharmaceutical demands, helping to prevent essential medication shortages or unavailability. As well, the need for recalls can be more quickly determined based on focused adverse drug reactions, which are noted to occur.

Insurance companies 24, health organizations 28 such as employers' health organizations, workers' compensation providers, private third party payers, PPO's, HMO's, MCO's 20, Medicare programs, life insurance companies, and the like, can monitor information to immediately determine needless prescription duplications, potential drug interactions, and multi-source interstate prescriptive medication abuse to thereby significantly reduce insurance costs.

Pharmacies 26 may check to personally verify the drug usage of each purchaser to immediately detect problems related to abuse, fraud, and misuse of medications. Pharmacies require a more precise method of monitoring the efficiency of the distribution of the more than three billion prescriptive medications they fill each year. The number of chain pharmacies has now risen to approximately 35,000 stores. The ability of pharmacies 26 to provide the highest quality service is placing a strain on staffing and the delivery of rapid, timely and accurate products. Pharmacists are constantly challenged to circumvent duplication, abuse, fraud, and misuse of these medications while providing a cost effective medication delivery system. In the present health system the wide availability of pharmaceuticals from different pharmacies raises the risks of negative drug interactions and its associated destructive medical outcome. Pharmaceutical information control organization 12 can flag these issues in real time, thereby completely preventing or at least minimizing their occurrences. Pharmaceutical information control organization 12 reduces or eliminates reliance on poorly trained pharmacy technicians or assistants in ensuring compliance with the regulatory agency demands in the accurate delivery of pharmaceuticals.

Physicians 18 and other healthcare providers are at risk every time they prescribe a drug. These physicians, seeking to provide their patients with the best possible healthcare possible, do not currently have a vehicle for ensuring they have an accurate view of their patients' use of prescription drugs. Information about prescriptive medications from specialists or other referral services may not be communicated appropriately. Patients may not remember prescriptive medications they are taking, forgetting about them completely or not being able to pronounce them. Patients with regular prescriptive medication patterns can empower physicians to proactively deal with potential abuse problems. Pharmaceutical information control organization 12 can also provide audit information that helps protect the professional from lawsuits and other potential liabilities. Physicians or their staff can also interact with patients 16 through information control organization 12, if desired. As well, physicians and/or their staff can keep records of patients in the system as well as provide researchers valuable information about the effects of prescriptive medications on literally hundreds of millions of patients.

Hospitals' 30 therapeutics, e.g., emergency room, often requires administration of medications on an acute and subacute basis with little or no knowledge of each patient's outpatient medication profile. Pharmaceutical information control organization 12 provides this vital data in a manner that will change the hospital medication delivery system in a dramatic fashion. The added information immediately reduces costs, adverse drug reactions, and eliminates the risks of facilitating drug abuse and misuse.

Application products and industry service providers 32, such as healthcare informatics providers, may use industry standard XML interfaces W3C that may define a dialect of SGML suitable for use on the World-Wide Web. SGML provides a generic markup language for representing documents and/or other data. SGML is an International Standard that describes the relationship between a document's content and its structure. SGML allows document-based information to be shared and reused across applications and computer platforms in an open, vendor-neutral format. SGML is sometimes compared to SQL, in that it enables companies to structure information in documents in an open fashion, so that it can be accessed or reused by any SGML-aware application across multiple platforms. SGML is defined in "ISO 8879:1986 Information processing—Text and office systems—Standard Generalized Markup Language (SGML)," an ISO standard produced by JTC 1/SC 18 and amended by "Amendment 1:1988." Unlike other common document file formats that represent both content and presentation, SGML represents a document's content data and structure (interrelationships among the data). Removing the presentation from content establishes a neutral format. SGML documents and the information within can easily be reused by publishing and non-publishing applications. SGML identifies document elements such as titles, paragraphs, tables, and chapters as distinct objects, allowing users to define the relationships between the objects for structuring data in documents. The relationships between document elements are defined in a Document Type Definition (DTD). This is roughly analogous to a collection of field definitions in a database. Once a document is converted into SGML and the information has been 'tagged,' it becomes a database-like document. It can be searched, printed or even programmatically manipulated by SGML-aware applications. If desired, secure access applets will allow informatics providers to integrate their products and services to include data access from pharmaceutical information control organization 12 in a seamless fashion. Thus, pharmaceutical information control organization 12 creates an independent utility service that adds value to application products and other service providers 32 while maintaining the overall goal of benefiting the public.

Thus, healthcare informatics and applications (such as physician practice management systems or Pharmacy systems) will be provided vehicles to securely access and interact with pharmaceutical information control organization 12 using industry standards such as XML and security tools. As appropriate, pharmaceutical information control organization 12 may provide secure applets that will make it easier to integrate computer interactions with pharmaceutical information control organization 12, as well as minimize the development costs associated with interfacing these applications.

Figure 2:
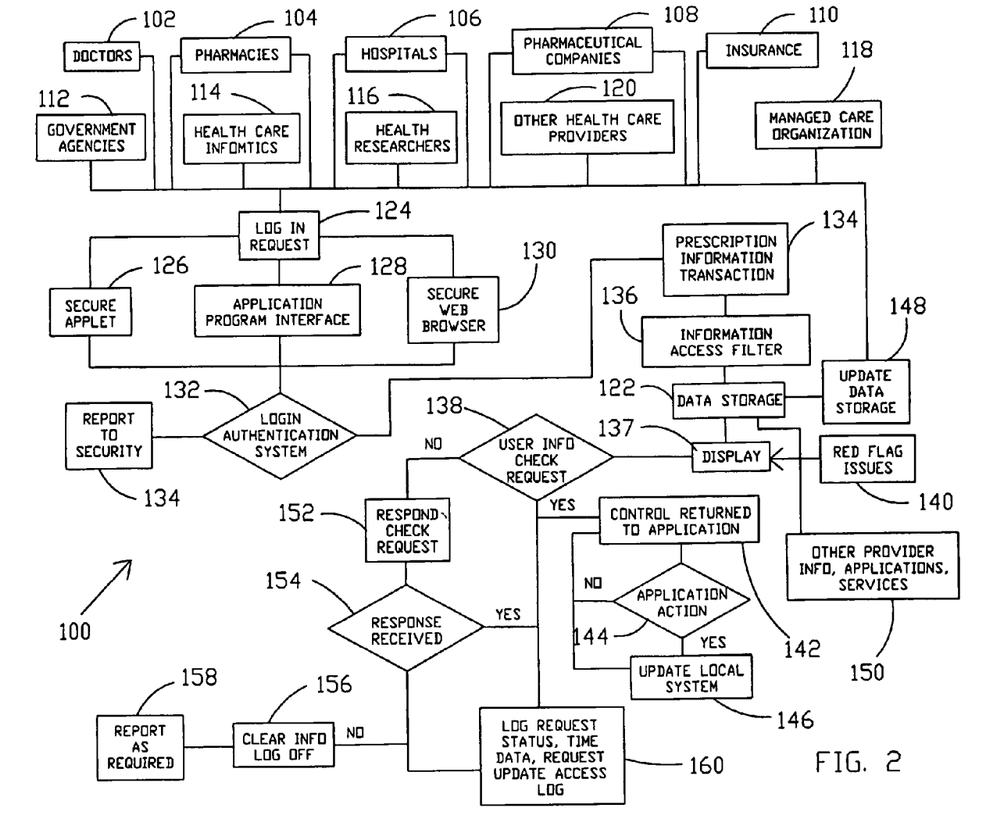
FIG. 2 is a block diagrammatic view showing another flow diagram of operation in accord with the present invention.

FIG. 2 discloses a presently preferred pharmaceutical information flow diagram 100 for a method of operation of pharmaceutical information control organization 12 in accord with the present invention. A plurality of entities, networks, and organizations may be utilized in accord with the present invention including doctors 102. Pharmacies 104 include pharmacies that are affiliated with each other as well as pharmacies that are unaffiliated with each other. Other entities include hospitals 106, pharmaceutical companies 108, insurance companies 110 (which may include health or life insurance companies or any other type of insurance companies), government agencies 112, health care informatics companies 114, health researchers 116, managed care organizations 118, and other healthcare providers 120. Such users may typically maintain their own database(s) of information as well as desire to access the overall information concerning each patient's pharmaceutical information, which is not presently available. In a preferred embodiment, the present invention provides that data storage 122 is able to access the databases of the above-listed entities and/or other member organizations as needed and/or store the corresponding pharmaceutical data in data storage 122 which is external to each entity's database(s). Thus, the present invention may be implemented using various types of data storage and data access including distributed searchable databases throughout the entities listed above whereby selected pharmaceutical data access to each database is available to data storage 122 and/or the above-listed entities, and/or a composite data storage 122 that is external with respect to the databases of the above entities but includes the relevant pharmaceutical data within each of the above entity's database(s). Data storage 122 provides a scalable, robust data store that maintains all pertinent information about prescriptive medication activities. Data storage 122 preferably has the ability to allow the software schemas to be changed without disruption of system 100.

In a preferred embodiment, when pharmaceutical data is needed by entities 102-120, or other suitable entities, then a login request is made as indicated at 124. The login request may be made through one or more different types of computer network interconnections, three possibilities of which are in FIG. 2. However, other types computer connections are also possible. A secure applet may be utilized as indicated at 126. The applet executes and initiates the login procedure. The applet may typically be supplied by pharmaceutical information control organization 12 or a third party vendor. Applets are Java programs, which can be distributed as an attachment in a World-Wide Web document and executed in a Java-enabled web browser. Web browsers can also be extended with plugins though these differ from applets in that they usually require manual installation and are platform specific. Server-side Java programs, which may be called servlets, may also be utilized.

Alternatively, or in conjunction therewith, an application program interfaces (API) may be utilized to effect the login as indicated at 128. The API is the interface (calling conventions) by which an application program accesses the pharmaceutical data. An API may typically be defined as source code level and provides a level of abstraction between the application and the kernel (or other privileged utilities) to ensure the portability of the code. The API can provide an interface between a high level language and lower level utilities and services which were written without consideration for the calling conventions supported by compiled languages. In this case, the API's main task may be the translation of parameter lists from one format to another and the interpretation of call-by-value and call-by-reference arguments in one or both directions.

As another option, a consumer accessing pharmaceutical information control organization 12 may utilize a secure web browser as indicated at 130 to initiate the login. By web browser it is meant a program which allows a person to read hypertext. The browser gives some means of viewing the contents of nodes (or "pages") and of navigating from one node to another.

Login authentication system 132 is provided to authenticate the validity of the login to provide verification of the identity of a person/entity or process that is attempting to access pharmaceutical information control organization 12. Authentication verifies that messages really come from their stated source. Various means of authentication may be utilized including login/password, biometrics, digital signatures, public and private digital encryption keys, digital certificates, and the like. The login process will identify the user and restrict the type of data transmitted according to the predetermined data sets that the particular user may access. If the login step is not successful, then the attempted login is automatically reported to security as indicated at 134.

Various types of security information may be stored by pharmaceutical information control organization 12 within data storage 122 or elsewhere. Such information may typically include the login name, login password, an optional biometric identifier, authentication of the user, authorized data set access for each user, authorized types of information transactions, an information log of access attempts (both successful and unsuccessful, an information log of transaction attempts (both successful and unsuccessful), encryption keys, digital signatures, and application programming interfaces where possible.

Assuming login process is successful, then the user may request a pharmaceutical information transaction as indicated at 134. Such transactions may be of various types and include searches, updates, selecting specific information, displaying information, and the like. The so-determined pharmaceutical information is available in the appropriate context via the secure applet, API, and/or browser as discussed hereinbefore in connection with the login as indicated at 126, 128, and 130. In this manner, current prescriptive medication information may be requested. The various programs discussed above and/or others may be used to select specific types of data for transfer as indicated at information access filter 136, and to send data either to or from the computer system of pharmaceutical information control organization 12, and change the format of the data as needed between that used by the computer software of pharmaceutical information control organization 12 and the user software.

Various types of data may be stored and/or obtained such as the doctor name, the doctor DEA number, patient name, patient ID (e.g., SS#, passport #, driver's license #, etc.), patient address, city, state, zip, patient phone number, drugs prescribed, dosage, frequency, start/end date, duration, quantity, number refills, whether substitution is allowed, generic allowed, notes, aberrant use flag, date prescription filed, place prescription filled, pharmacist name, pharmacist phone number, pharmacist DEA number, and application programming interfaces utilized.

The request of data from the pharmaceutical transaction 134 is sent to data storage 122. Various types of transactions may be utilized such as updates, key word or other types of searches, name searches, drug type searches, and/or other types of searches based on the above-listed types of data stored and/or other types of data which may be stored. Transactions include authentication transactions, display of active medication history, display of inactive medication history, and display of complete medication history. The display may be made by a patient identifier, patient name, date, drug name, doctor prescribing the medication, pharmacy, geography (city, state, zip code), by phone number, and/or by aberrant use flag. Other transactions may include adding a new record, update/change a record, add log entry, update log entry, display log entries, approve prescriptive medication, decline prescriptive medication, aberrant use flag true or false, accept results, decline results, logon, logoff, time out for inactivity, time out for disconnection, encryption, and creating reports.

The data is filtered as to availability for the particular user, as indicated at 136. The data may be sent for display 137 and/or printing. Data may be retrieved for updating data storage 122 as indicated at 148. The user may then check the data or the user's application in a preset time frame as indicated at 138. Depending on the type of user, red flag issues may be indicated. For instance, if a pharmacist is checking on a prescriptive medication prior to dispensing the prescriptive medication, a red flag as indicated at 140 may be issued if the prescription presents a problem, e.g., is a conflicting type of drug (contraindicated prescriptive medication) or perhaps a similar type of drug which in combination with a previous prescriptive medication might be harmful to the consumer. Red flags may be issued as a result of automatic or manual operation. The system 100 and/or the pharmacist and/or the doctor may require or suggest declining or approving the prescriptive medication, and otherwise add notes, comments, and flags, as desired. Assuming the user reviews and checks the information supplied within the time frame, the control may be returned to the user's application as indicated at 142 which may require action as indicated at 144 such as updating 146 either a local system and/or data storage 122. Updating of data storage 122 may be programmed to occur at any time, depending on system operation, and may occur outside of or during the transaction process as indicated at 148 whereby a connection is provided directly to the databases of the subscribers 102-120. Data storage 122 may also receive other provider information for use with applications and services as indicated at 150.

In a presently preferred embodiment, if the user does not respond to the check request within a desired time frame, if necessary, such as by stating whether the prescriptive medication is approved/declined or so forth, such as after the pharmacist has checked a new request to fill a prescription with respect to the requesters medical history, then the system resends the request to check the data as indicated at 152. Thus, the system seeks to know whether any new prescription is filled and the various data associated with the new prescriptive medication. Depending on the type of entity, different types of data may be requested. For instance, for the hospital, information as to treatment and prescriptive medications may be requested by the system. If no response is received as indicated at 154, then the data such as displayed data is cleared from the screen, the user is automatically logged off at 156, and a report is sent as may be required by an oversight agency as indicated at 158. For instance, there may be a requirement to enter new data related to prescriptive medications, whether prescriptions are filled or declined, and so forth. In either case, a log is made of the request, status, time, data, requester, as indicated at 160, and the access log is updated.

Pharmaceutical information control organization 12 will provide appropriate levels of reporting, as desired, to any selected oversight body or committee, as well as other healthcare members as appropriate and necessary. Such reporting/informational access can include up-to-date patient prescriptive medication information to their primary care physician or pharmacy, comparisons for potential drug interactions, and/or emergency information access.

For hosting and management, deployment of computer connections with pharmaceutical information control organization 12 is preferably made via a secure, redundant, hosted environment. Operational and administrative personnel will need to pass rigorous screening processes, and will only have access to information as is contextually necessary.

The foregoing disclosure and description of the invention is therefore illustrative and explanatory of one or more presently preferred embodiments of the invention and variations thereof, and it will be appreciated by those skilled in the art that various changes in the design, organization, order of operation, means of operation, equipment structures and location, methodology, and use of mechanical equivalents, as well as in the details of the illustrated construction or combinations of features of the various elements, may be made without departing from the spirit of the invention. As well, the drawings are intended to describe the concepts of the invention so that the presently preferred embodiments of the invention will be plainly disclosed to one of skill in the art but are not intended to be manufacturing level drawings or renditions of final products and may include simplified conceptual views as desired for easier and quicker understanding or explanation of the invention. As well, the relative arrangement of the components may be greatly different from that shown and still operate well within the spirit of the invention as described hereinbefore and in the appended claims. It will be seen that various changes and alternatives may be used that are contained within the spirit of the invention. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A pharmaceutical information control system comprising:

a data input/output station for use by doctors, affiliated pharmacies, unaffiliated pharmacies, hospitals, pharmaceutical companies, insurance companies, government agencies, health care informatics companies, health researchers, managed care organizations, healthcare providers and combinations thereof for entering and receiving prescription drug information, the data input/output station in association with an entity database associated with a plurality of entities, networks and organizations or a combination thereof at various positions within the prescriptive medication process that maintain databases of pharmaceutical data including prescription drug use data, each database having a format that provides for access control and management capabilities for individual users as dictated by each of the plurality of entities, networks and organizations, legislation or a combination thereof, wherein the plurality of entities, networks and organizations comprise doctors, affiliated pharmacies, unaffiliated pharmacies, hospitals, pharmaceutical companies, insurance companies, government agencies, health care informatics companies, health researchers, managed care organizations, healthcare providers and combinations thereof, a data storage device for accessing the entity databases of the plurality of entities, networks and organizations and storing entity information, application programming interfaces and service components to enable the integration of an entity system, wherein the application programming interfaces and service components provide managed access and sharing of contextually relevant information from the plurality of entities, networks and organizations, and provide business logic and workflow for the contextual management, collection, assembly, reporting, alerting, sharing or a combination thereof of information, an information access filter for mapping the format of the data between the data format used by the entity database and the format used by the data storage device for selecting pharmaceutical data for creating a complete prescriptive history of an individual, and for maintaining the privacy of information related to the individual, wherein the data storage is adapted for communication with the information access filter and the application program interfaces and service components, for analyzing the information in the data storage device and providing analysis thereof to the application program interfaces and service components, wherein the application programming interfaces and service components are in operative association with the data storage device, the entity database and a login authentication system for validating the access of the user and for the user to request a pharmaceutical transaction, wherein the pharmaceutical transaction is communicated to the data storage device for storage, and wherein the data storage device is adapted to acquire the entity information and prior pharmaceutical transactions related to the pharmaceutical transaction from the data input/output station, thereby acquiring an updated complete prescriptive history related to the current pharmaceutical transaction and analyzing the updated complete prescriptive history by generating one or more patterns that detect prescription duplication or multi-source prescription abuse for providing at least one of: the analysis of the information, or a recommendation to the user, thereby recommending the approval of the pharmaceutical transaction, the declination of the pharmaceutical transaction, application of notes, comments or flags to the pharmaceutical transaction or a combination thereof to the data input/output station.

2. The pharmaceutical information control system of claim 1 wherein the user implements the pharmaceutical data to verify the complete prescriptive history of a patient.

3. The pharmaceutical information control system of claim 1 wherein the pharmaceutical data for each of the prescriptive medication purchases comprises a name of purchaser, an address of the purchaser, a drug prescribed, a quantity of said drug, a dosage of said drug, a pharmacist name, a doctor name or a combination thereof.

4. A pharmaceutical information control system comprising:
   a data input/output station for use by doctors, affiliated pharmacies, unaffiliated pharmacies, hospitals, pharmaceutical companies, insurance companies, government agencies, health care informatics companies, health researchers, managed care organizations, healthcare providers and combinations thereof for entering and receiving prescription drug information,
   the data input/output station in association with an entity database associated with a plurality of entities, networks and organizations or a combination thereof at various positions within the prescriptive medication process that maintain databases of pharmaceutical data including prescription drug use data, each database having a format that provides for access control and management capabilities for individual users as dictated by each of the plurality of entities, networks and organizations, and or legislation or a combination thereof,
   wherein the plurality of entities, networks and organizations comprise doctors, affiliated pharmacies, unaffiliated pharmacies, hospitals, pharmaceutical companies, insurance companies, government agencies, health care informatics companies, health researchers, managed care organizations, healthcare providers and combinations thereof,
   a data query device for accessing the entity databases of the plurality of entities, networks and organizations and providing the entity information to data input/output station,
   application programming interfaces and service components to enable the integration of an entity system,
   wherein the application programming interfaces and service components provide managed access and sharing of contextually relevant information from the plurality of entities, networks and organizations, and provide business logic and workflow for the contextual management, collection, assembly, reporting, alerting, sharing or a combination thereof of information,
   an information access filter for mapping the format of the data between the data format used by the entity database and the format used by the data query device for selecting pharmaceutical data for creating a complete prescriptive history of an individual, and for maintaining the privacy of information related to the individual,
   wherein the data query device is adapted for communication with the information access filter and the application program interfaces and service components, for analyzing the information queried by the data query device and for providing analysis thereof to the application program interfaces and service components,
   wherein the application programming interfaces and service components are in operative association with the data query device, the entity database and a login authentication system for validating the access of the user and for the user to request a pharmaceutical transaction via the data input/output station, wherein the pharmaceutical transaction is communicated via the data query device to the data input/output station,
   and wherein the data query device is adapted to acquire the entity information and prior pharmaceutical transactions related to the pharmaceutical transaction, thereby acquiring an updated complete prescriptive history related to the current pharmaceutical transaction and analyzing the updated complete prescriptive history by generating one or more patterns that detect prescription duplication or multi-source prescription abuse for providing at least one of: the analysis of the information, or a recommendation to the data input/output station, thereby recommending the approval of the pharmaceutical transaction, the declination of the pharmaceutical transaction, application of notes, comments or flags to the pharmaceutical transaction or a combination thereof to the data input/output station.

5. The pharmaceutical information control system of claim 4 wherein the user implements the pharmaceutical data to verify the complete prescriptive history of a patient.

6. The pharmaceutical information control system of claim 4 wherein the pharmaceutical data for each of the prescriptive medication purchases comprises a name of purchaser, an address of the purchaser, a drug prescribed, a quantity of said drug, a dosage of said drug, a pharmacist name, a doctor name or a combination thereof.

7. A pharmaceutical information control system comprising:
   at least one entity database, at least one defined entity, a data storage device, a software interface for each entity database, and a filter for conversion between the entity database and the storage device,
   such that the entity database is associated with the at least one defined entities, networks and organizations at various points within a prescriptive medication process that maintain databases of pharmaceutical data including prescription drug use data, each database having a format that provides for access control and management capabilities for individual users as dictated by each of the at least one defined entities, networks and organizations, legislation or a combination thereof,
   wherein the at least one defined entities, networks and organizations comprise doctors, affiliated pharmacies, unaffiliated pharmacies, hospitals, pharmaceutical companies, insurance companies, government agencies, health care informatics companies, health researchers, managed care organizations, healthcare providers and combinations thereof,
   the data storage device for accessing the entity databases of the at least one defined entities, networks and organizations and storing entity information,
   the software interface to enable the integration of an entity system, wherein the software interface provides managed access and sharing of contextually relevant information from the defined entities, networks and organizations, and provide business logic and workflow for the contextual management, collection, assembly, reporting, alerting, sharing or a combination thereof of information consistent with availability and satisfying legislative and corporate requirements and standards for data management, entity security, integration needs or combinations thereof, the filter for changing the format of the data between the data format used by the entity database and the format used by the data storage device for selecting pharmaceutical data for creating a complete prescriptive history of an individual, and for maintaining the privacy of information related to the individual, wherein the data storage device is adapted for communication with the filter and the software interface for analyzing the information in the data storage device and providing analysis thereof to the software interface, wherein the software interface is in operative association with the data storage device, the entity database and a login authentication system for validating the access of the user and for the user to request a pharmaceutical transaction, wherein the pharmaceutical transaction is communicated to the data storage device for storage, and wherein the data storage device is adapted to acquire the entity information and prior pharmaceutical transactions related to the pharmaceutical transaction, thereby acquiring an updated complete prescriptive history related to the current pharmaceutical transaction and analyzing the updated complete prescriptive history by generating one or more patterns that detect prescription duplication or multi-source prescription abuse for providing at least one of: the analysis of the information, or a recommendation to the user, thereby recommending the approval of the pharmaceutical transaction, the declination of the pharmaceutical transaction, application of notes, comments or flags to the pharmaceutical transaction or a combination thereof.

* * * * *